United States Patent
Britovsek et al.

(10) Patent No.: US 8,426,535 B2
(45) Date of Patent: *Apr. 23, 2013

(54) CHAIN GROWTH REACTION PROCESS

(75) Inventors: George Johan Peter Britovsek, London (GB); Steven A. Cohen, Naperville, IL (US); Vernon Charles Gibson, London (GB)

(73) Assignee: Ineos Europe Limited, Hampshire (GB)

( * ) Notice: Subject to any disclaimer, the term of this patent is extended or adjusted under 35 U.S.C. 154(b) by 380 days.

This patent is subject to a terminal disclaimer.

(21) Appl. No.: 12/801,741

(22) Filed: Jun. 23, 2010

(65) Prior Publication Data

US 2010/0331563 A1 Dec. 30, 2010

Related U.S. Application Data

(63) Continuation-in-part of application No. 11/476,206, filed on Jun. 28, 2006, now Pat. No. 7,767,771, which is a continuation of application No. 09/921,695, filed on Aug. 6, 2001, now Pat. No. 7,087,686.

(51) Int. Cl.
- *C08F 4/50* (2006.01)
- *C08F 4/76* (2006.01)
- *C08F 4/80* (2006.01)
- *B01J 31/00* (2006.01)
- *B01J 31/28* (2006.01)

(52) U.S. Cl.
USPC ........... 526/113; 526/114; 526/115; 526/116; 526/117; 526/161; 526/172; 526/160; 526/170; 526/169; 526/169.1; 502/129; 502/103; 502/152; 502/154

(58) Field of Classification Search ................. 526/113, 526/115, 116, 170, 161, 114
See application file for complete search history.

(56) References Cited

U.S. PATENT DOCUMENTS

| | | | |
|---|---|---|---|
| 3,252,958 A | 5/1966 | Giachetti et al. | |
| 4,063,009 A | 12/1977 | Ziegler et al. | |
| 4,308,369 A | 12/1981 | Shipley et al. | |
| 4,335,016 A | 6/1982 | Dombro | |
| 4,361,714 A * | 11/1982 | Langer et al. | 585/521 |
| 5,034,483 A | 7/1991 | Miro et al. | |
| 5,068,489 A | 11/1991 | Edwards et al. | |
| 5,221,774 A * | 6/1993 | Wu | 585/520 |
| 5,414,178 A | 5/1995 | Wu | |
| 5,449,850 A * | 9/1995 | Young et al. | 585/523 |
| 5,557,027 A | 9/1996 | Kemp | |
| 5,688,733 A | 11/1997 | Renkema et al. | |

(Continued)

FOREIGN PATENT DOCUMENTS

| | | |
|---|---|---|
| EP | 0 295 960 A1 | 12/1988 |
| EP | 0 464 744 A2 | 1/1992 |
| WO | WO 91/02707 A1 * | 3/1991 |

*Primary Examiner* — Rip A. Lee
(74) *Attorney, Agent, or Firm* — Nixon & Vanderhye

(57) ABSTRACT

A process is disclosed for the preparation of zinc alkyl chain growth products via a catalyzed chain growth reaction of an alpha-olefin on a zinc alkyl, wherein the chain growth catalyst system employs a group 3-10 transition metal, or a group 3 main group metal, or a lanthanide or actinide complex, and optionally a suitable activator. The products can be further converted into alpha-olefins by olefin displacement of the grown alkyls as alpha-olefins from the zinc alkyl chain growth product, or into primary alcohols, by oxidation of the resulting zinc alkyl chain growth product to form alkoxide compounds, followed by hydrolysis of the alkoxides.

7 Claims, 18 Drawing Sheets

U.S. PATENT DOCUMENTS

| | | |
|---|---|---|
| 6,245,869 B1 | 6/2001 | Debras et al. |
| 6,333,292 B1 | 12/2001 | Gibson et al. |
| 6,372,681 B1 | 4/2002 | Yamada et al. |
| 6,451,939 B1 | 9/2002 | Britovsek et al. |
| 6,461,994 B1 | 10/2002 | Gibson et al. |
| 6,521,724 B2 | 2/2003 | Arthur et al. .................... 526/89 |
| 6,583,237 B1 | 6/2003 | Imuta et al. |
| 7,087,686 B2 * | 8/2006 | Britovsek et al. ............. 526/113 |
| 7,767,771 B2 * | 8/2010 | Britovsek et al. ............. 526/113 |
| 7,964,681 B2 * | 6/2011 | Britovsek et al. ............. 526/161 |
| 2003/0119921 A1 * | 6/2003 | De Boer et al. ............... 518/715 |

* cited by examiner

CHAIN GROWTH REACTION PROCESS

CROSS-REFERENCES TO RELATED APPLICATIONS

This application is a Continuation-in-Part of application Ser. No. 11/476,206 filed Jun. 28, 2006, now U.S. Pat. No. 7,767,771, which is a continuation of application Ser. No. 09/921,695 filed Aug. 6, 2001, now U.S. Pat. No. 7,087,686, the entire contents of each of which are hereby incorporated by reference.

CHAIN GROWTH REACTION PROCESS

This invention relates to the preparation of zinc alkyls by the chain growth reaction of a lower olefin, especially ethylene, with a lower molecular weight zinc alkyl and more specifically to a chain growth process on zinc, catalysed by a catalyst system comprising a group 3-10 transition metal, group 3 main group metal, lanthanide or actinide complex, and optionally a suitable activator.

The reactivity of zinc alkyls (and zinc alkenyls) with lower olefins has been reported, see Journal of Organometallic Chemistry 1973, 60, p 1-10; Liebigs Ann. Chem. 1975, p 1162-75; Journal of Organometallic Chemistry 1981, 221, p 123-130. Di-tert-butyl zinc reacts with 2 equivalents of ethylene between −20 C and 75 C to give bis(3,3-dimethylbutyl) zinc, each zinc alkyl group effectively inserting only one ethylene molecule. Dialk-2-enylzinc compounds add to 2 equivalents of ethylene to give the dialk-4-enylzinc compounds, each zinc alkenyl group reacting with only one ethylene molecule. A second type of reaction between an alkyl zinc species and an olefin also is known. It involves an (α-haloalkyl)zinc intermediate reacting with an olefin to produce a cyclopropane product and is frequently referred to as the Simmons-Smith procedure [see *J. Am. Chem Soc.* 81, 4256 (1959); *Ibid,* 86, 1337, (1964); Org React., 20, 1-131 (1973).]

There have been no reports of the preparation of zinc alkyls by reaction of a lower olefin with lower molecular weight zinc alkyl, where more than one olefin inserts into an alkylzinc bond or where the chain growth process is catalysed by a catalyst system. These types of reactions would be examples of stoichiometric chain growth, the catalysed version is known in the field as catalysed chain growth. (See eq. 1, M=Zn)

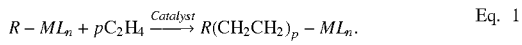

$$R - ML_n + pC_2H_4 \xrightarrow{Catalyst} R(CH_2CH_2)_p - ML_n. \quad \text{Eq. 1}$$

Catalysed chain growth of ethylene has been demonstrated for aluminium alkyls (M=Al in eq. 1), where an activated metallocene compound acts as the catalyst system. This is described in U.S. Pat. Nos. 5,210,338 and 5,276,220. According to the process described in U.S. Pat. No. 5,210,338, a catalyst system comprising metallocene halo-complexes of zirconium and hafnium and related complexes in combination with methylaluminoxane (MAO) produce aluminium alkyls, where the ethylene chain growth products are best described by the Schulz-Flory statistical distribution; polyethylene is a persistent co-product. The Schulz-Flory distribution is described by the formula $\chi_p = \beta/(1+\beta)^p$, where $\chi_p$ is the mole fraction containing p added ethylenes and $\beta$ is the Schulz-Flory distribution coefficient. According to the process described in U.S. Pat. No. 5,276,220, aluminum alkyl chain growth is catalysed at mild temperatures and pressures with a catalyst system comprising an activated actinide metallocene compound. In addition, the ethylene chain growth products from the process described in U.S. Pat. No. 5,276,220 provides a Poisson-like alkyl chain length distribution and avoids formation of a polymeric co-product. A Poisson chain length statistical distribution is described by the formula $\chi_p = (x^p e^{-x})/p!$, where $\chi_p$ is the mole fraction with p added ethylenes and x is the Poisson distribution coefficient equal to the average number of ethylenes added per Al—C bond. As described in these patents, the catalysed ethylene chain growth processes with aluminium alkyls operate at dramatically lower pressures and temperatures than does the non-catalysed, stoichiometric ethylene chain growth on aluminium alkyls (100-200° C., 2000-4000 psi ethylene).

A number of ethylene chain growth processes on aluminium alkyls have been found to be particularly useful in the production of linear alpha-olefins and linear alcohols. Alpha-olefins can be generated from alkyl chain growth on aluminium, by displacement of the olefin product with ethylene either simultaneous with the chain growth reaction to yield a Schulz-Flory-like distribution of products or in a second, separate step. It is found that the catalysed chain growth process gives more highly linear alkyl groups than those produced under the more forcing conditions required to effect the uncatalysed chain growth reaction.

However, in certain instances, the physical and chemical characteristics of the aluminium alkyl species present in the processes described above limit the usefulness of the known catalysed chain growth processes. Aluminium alkyl compounds form compositionally complex monomeric and dimeric species that can be difficult to separate from one another or from the product olefins. They can react with product olefins to make unwanted by-products and they are highly reactive, even with relatively unreactive chemicals such as carbon dioxide, and may, over time, inactivate the metallocene chain growth catalyst systems, thereby greatly increasing their cost.

It is therefore desirable to develop catalysed chain growth processes that do not possess the limitations of the known processes using aluminium alkyls, or for which the limitations are substantially lessened.

We have discovered that some of the above problems can be successfully addressed by using zinc alkyl compounds instead of aluminium alkyls. In accordance with the present invention therefore, there is provided a process for the preparation of zinc alkyl chain growth products via a catalysed chain growth reaction of an alpha-olefin on a zinc alkyl, comprising contacting the zinc alkyl with a chain growth catalyst system which employs a group 3-10 transition metal, or a group 3 main group metal, or a lanthanide or actinide complex, and optionally a suitable activator. This zinc alkyl chain growth product may be a single material or a mixture of compounds, and may be used to prepare alpha olefins, alcohols, lubricants, speciality chemicals, and pharmaceuticals, catalyst systems, polymeric intermediates, or polymeric materials.

Also provided is a process for the preparation of alpha-olefins by the catalysed chain growth reaction of an alpha-olefin on a zinc alkyl, followed by olefin displacement of the grown alkyls as alpha-olefins from the zinc alkyl chain growth product, where the chain growth catalyst system employs a group 3-10 transition metal, group 3 main group metal, lanthanide or actinide complex, and optionally a suitable activator.

Also provided is a process for the preparation of primary alcohols by the chain growth reaction of alpha-olefin on a zinc alkyl, oxidation of the resulting zinc alkyl chain growth product to form alkoxide compounds, followed by hydrolysis of the alkoxides to produce primary alcohols, where the chain growth catalyst system employs a group 3-10 transition metal, group 3 main group metal, lanthanide or actinide complex, and optionally a suitable activator.

The invention also provides in another aspect compositions of alkyl zinc complexes where the alkyl groups follow a substantially Poisson-like statistical distribution of chain lengths up to about 200 carbon atoms, and compositions of alkyl zinc complexes where the alkyl groups follow a substantially Schulz-Flory-like statistical distribution of chain lengths up to about 50,000 carbon atoms.

Examples of olefins suitable for chain growth include, but are not limited to, $C_2$ to $C_{26}$ alpha-olefins, and mixtures thereof, with $C_2$ to $C_{16}$ linear alpha-olefins being the preferred olefins. For the preparation of highly linear zinc alkyl chain growth product, and materials derived therefrom such as linear alpha olefins and linear primary alcohols, ethylene is the most preferred olefin. Depending upon the intended use, it may be desirable to produce, via the present invention, a Schulz-Flory-like distribution of grown alkyl species, while in other instances a Poisson-like distribution of grown zinc alkyl species may be advantageous. Other product distributions and distributions intermediate between those characterized by Schulz-Flory and Poisson statistics can be achieved by those skilled in the art by manipulating the catalyst and/or the process conditions. The skeletal architecture of the chain grown alkyls and their derivatives similarly can be varied by skillful control of the catalyst(s), olefin feedstocks, initial alkylzinc species, and the reaction conditions. For example, to produce a polymeric intermediate containing a low temperature, ethylene-based elastomer or plastomer structure, one could employ a suitable bis(imine)nickel or Pd catalyst such as [1,4-bis(2,6-diisopropylphenyl)-1,4-diaza-2,3-dimethylbutadiene]nickel(II) bromide together with ethylene with or without an additional comonomer, and an alkyl zinc species, the resulting Zn-capped material being useful for making AB-type block copolymers.

The catalysed chain growth reaction can be performed under a range of process conditions that are readily apparent to those skilled in the art: as a homogeneous liquid phase reaction in the presence or absence of an inert hydrocarbon diluent such as toluene or heptanes; as a two-phase liquid/liquid reaction; as a slurry process where the catalyst and/or the reaction products have little or no solubility or are supported; as a bulk process in which essentially neat zinc alkyls or olefins serve as the dominant medium; as a gas-phase process in which volatile zinc alkyl species and olefins contact the catalyst from a gaseous state. In certain instances, the chain growth reaction can be carried out in the presence of the products of subsequent reactions of the chain grown zinc alkyls, a non-limiting example being tetradecene and other chain grown linear alpha olefins constituting part or all of the diluent utilized in liquid phase (catalysed) addition of ethylene to dibutylzinc. The catalysed chain growth reactions may be performed in the known types of gas-phase reactors (such as vertically or horizontally stirred-bed, fixed-bed, or fluidised-bed reactors,) liquid-phase reactors (such as plug-flow, continuously stirred tank, or loop reactors,) or combinations thereof.

Reaction temperatures for the catalysed chain growth reactions may vary from sub-ambient temperatures (below 20° C.) to approximately 200° C. Pressures of ethylene may be varied from about 1 psig to about 5000 psig, although it is generally advantageous to operate at pressures below 1500 psig.

Suitable zinc alkyl feed compounds for the chain growth are any species or mixture of species containing the R'R"CH—Zn— or R'R"C—Zn— moieties, where R' and R" are independent and can be hydrogen, hydrocarbyl, silyl, or substituted hydrocarbyl group; R' and R" may be connected and thus form a cyclic species; in the case of R'R"C—Zn—, the C bonded to the Zn is unsaturated [non-limiting examples of R'R"C—Zn— compounds being di-phenyl-Zn and $(C_5H_5)$ ZnEt]. Compounds containing the R'R"CH—Zn— moiety include dialkyl zincs and alkyl zinc hydrides, which can be represented by the formula $R_mZnH_n$ where m is 1 or 2 and n is 0 or 1, m+n=2, and each R is independently $C_1$ to $C_{30}$ alkyl. Mixtures of these compounds can be used. Specific non-limiting examples of suitable feed compounds include dimethylzinc, diethylzinc, di-n-butylzinc, di-n-hexylzinc, dibenzylzinc, di-n-decylzinc, di-n-dodecylzinc, and the like. Preferred zinc alkyl feedstocks for the chain growth process are low molecular weight zinc alkyls having alkyl groups with even carbon numbers and especially diethylzinc and di-n-butylzinc. Diethylzinc is commercially available while routes for preparing other dialkylzinc are well known in the literature and include thermal disproportionation of alkyl zinc halides, alkylation of zinc salts by alkyl aluminium compounds, and metal exchange of Zn with dialkylmercury compounds.

The chain growth catalyst system employs a group 3-10 transition metal, group 3 main group metal, lanthanide or actinide complex, and optionally a suitable activator.

Suitable complexes are the metallocenes, which may contain at least one cyclopentadienyl-based ring ligands. For the purposes of this patent specification the term "metallocene" is defined as containing one or more unsubstituted or substituted cyclopentadienyl or cyclopentadienyl moiety in combination with a group 3-6 transition metal, a group 3 main group metal, a lanthanide or an actinide. In one embodiment the metallocene catalyst component is represented by the general formula $(C_p)_mMR_nR'_p$ wherein at least one $C_p$ is an unsubstituted or, preferably, a substituted cyclopentadienyl ring, a substituted or unsubstituted ring system such as an indenyl moiety, a benzindenyl moiety, a fluorenyl moiety or the like, or any other ligand capable of η-5 bonding such as borolles or phospholes; M is a Group 4, 5 or 6 transition metal, a lanthanide or an actinide; R and R' are independently selected halogen, hydrocarbyl group, or hydrocarboxyl groups having 1-20 carbon atoms or combinations thereof; m=1-3, n=0-3, p=0-3, and the sum of m+n+p equals the oxidation state of M, preferably m=2, n=1 and p=1. The Cp can be substituted with a combination of substituents, which can be the same or different. Non limiting examples of substituents include hydrogen or a linear, branched or cyclic alkyl, alkenyl or aryl radical having from 1 to 20 carbon atoms.

In another embodiment the metallocene catalyst component is represented by the formulas:

, or

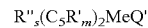

wherein Me is a Group 4, 5 or 6 transition metal, a lanthanide or an actinide; at least one $C_5R'_m$ is a substituted cyclopentadienyl, each R', which can be the same or different is hydrogen, alkyl, alkenyl, aryl, alkylaryl or arylalkyl radical having from 1 to 20 carbon atoms or two carbon atoms joined together to form a part of a substituted or unsubstituted ring or rings having 4 to 20 carbon atoms, R" is one or more of or a combination of a carbon, a germanium, a silicon, a phosphorous or a nitrogen atom containing radical bridging two ($C_5R'_m$) rings, or bridging one ($C_5R'_m$) ring to M, when p=0 and x=1 otherwise "x" is always equal to 0, each Q which can be the same or different is an aryl, alkyl, alkenyl, alkylaryl, or arylalkyl radical having from 1 to 20 carbon atoms, halogen, or alkoxides, Q' is an alkylidene radical having from 1-20 carbon atoms, s is 0 or 1 and when s is 0, m is 5 and p is 0, 1 or 2 and when s is 1, m is 4 and p is 1.

Preferred metallocenes are bis(pentamethylcyclopentadienyl)zirconium dichloride, bis(pentamethylcyclopentadienyl)hafnium dichloride, bis(tetramethylcyclopentadienyl) zirconium dichloride, (pentamethylcyclopentadienyl) zirconium trichloride, (tetramethylcyclopentadienyl)(t-butylamido)(dimethylsilane)titanium dimethyl, and (pentamethylcyclopentadienyl)(cyclopentadienyl)zirconium dichloride.

Other suitable complexes are the group 3-10 transition metal, group 3 main group metal, lanthanide or actinide complexes containing a neutral, monoanionic, dianionic ligands, which can be mondentate, bidentate, tridentate or tetradentate, and which comprise at least one N, P, O or S atom. Non-limiting examples of such complexes are described in WO 96/23010, WO 97/02298, WO 98/30609, WO 99/50313, WO 98/40374, WO 00/50470, WO 98/42664, WO 99/12981, WO 98/27124, WO 00/47592, WO 01/58966 and our own co-pending applications PCT 02/02247 and PCT 02/02144.

A preferred class of transition metal complexes are represented generically by the Formula (I):

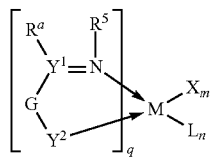

wherein M is Y[II], Y[III], Sc[II], Sc[III], Ti[II], Ti[III], Ti[IV], Zr[II], Zr[III], Zr[IV], Hf[II], Hf[III], Hf[IV], V[II], V[III], V[IV], Nb[II], Nb[III], Nb[IV], Nb[V], Ta[II], Ta[III], Ta[IV], Cr[II], Cr[III], Mn[II], Mn[III], Mn[IV], Fe[II], Fe[III], Ru[II], Ru[III], Ru[IV], Co[II], Co[III], Rh[II], Rh[III], Ni[II], Pd[II], X represents an atom or group covalently or ionically bonded to the transition metal M; $Y^1$ is C or P($R^c$); $Y^2$ is —O($R^7$), —O (in which case the bond from O to M is covalent), —C($R^b$)=O, —C($R^b$)=N($R^7$), —P($R^d$)=N($R^7$) or —P($R^b$)($R^d$)=O; $R^a$, $R^b$, $R^c$, $R^d$, $R^5$ and $R^7$ are each independently selected from hydrogen, halogen, hydrocarbyl, substituted hydrocarbyl, heterohydrocarbyl, substituted heterohydrocarbyl or $SiR'_3$ where each R' is independently selected from hydrogen, halogen, hydrocarbyl, substituted hydrocarbyl, heterohydrocarbyl and substituted heterohydrocarbyl, and any adjacent ones may be joined together to form a ring; G is either a direct bond between $Y^1$ and $Y^2$, or is a bridging group, which optionally contains a third atom linked to M when q is 1; L is a group datively bound to M; n is from 0 to 5; m is 1 to 3 and q is 1 or 2.

One preferred complex is represented by the general formula (II):

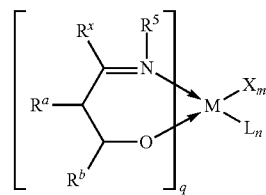

wherein $R^x$ is selected from hydrogen, halogen, hydrocarbyl, substituted hydrocarbyl, heterohydrocarbyl, substituted heterohydrocarbyl or $SiR'_3$ where each R' is independently selected from hydrogen, halogen, hydrocarbyl, substituted hydrocarbyl, heterohydrocarbyl and substituted heterohydrocarbyl, and all other substituents are as defined above. In the complex of Formula (II), M is preferably a Group IV metal, particularly Ti, Zr, a Group VI metal, particularly Cr, or a Group VIII metal, particularly Ni, Co, or Pd. Preferably $R^a$ and $R^b$ are joined together to form a phenyl, which is preferably substituted. Preferred substituents are $C_1$-$C_6$ alkyl or $C_6$-$C_{24}$ aryl or aralkyl. In particular, the phenyl group may be substituted at the position adjacent the oxygen linkage with a t-butyl group or an anthracenyl group, which may itself be substituted.

A further preferred complex is that of Formula (III):

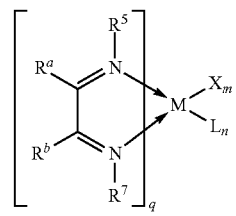

wherein M is Cr[II], Cr[III], Mn[II], Mn[III], Mn[IV], Fe[II], Fe[III], Ru[II], Ru[III], Ru[IV], Co[II], Co[III], Rh[II], Rh[III], Ni[II], Pd[II], Cu[I], Cu[II]; X represents an atom or group covalently or ionically bonded to the transition metal M; $R^a$ and $R^b$ are each independently selected from hydrogen, halogen, hydrocarbyl, substituted hydrocarbyl, heterohydrocarbyl, substituted heterohydrocarbyl or $SiR'_3$ where each R' is independently selected from hydrogen, halogen, hydrocarbyl, substituted hydrocarbyl, heterohydrocarbyl and substituted heterohydrocarbyl, and $R^a$ and $R^b$ may be joined together to form a ring; $R^5$ and $R^7$ are each as defined above; and L is a group datively bound to M; n is from 0 to 5; m is 1 to 3 and q is 1 or 2. Preferably M is Fe, Ni or Pd.

A particularly preferred complex has the following Formula (IV):

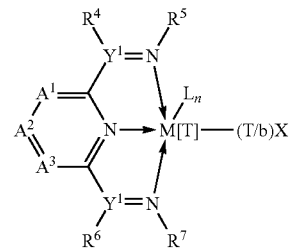

wherein M[T] is Ti[II], Ti[III], Ti[IV], Zr[II], Zr[III], Zr[IV], Hf[II], Hf[III], Hf[IV], V[II], V[III], V[IV], Nb[II], Nb[III], Nb[IV], Nb[V], Ta[II], Ta[III], Ta[IV], Cr[II], Cr[III], Mn[II], Mn[III], Mn[IV], Fe[II], Fe[III], Ru[II], Ru[III], Ru[IV], Co[II], Co[III], Rh[II], Rh[III], Ni[II], Pd[II]; X represents an atom or group covalently or ionically bonded to the transition metal M; T is the oxidation state of the transition metal M and b is the valency of the atom or group X; $Y^1$ is C or $P(R^c)$, $A^1$ to $A^3$ are each independently N or P or CR, with the proviso that at least one is CR; R, $R^c$, $R^4$ and $R^6$ are each independently selected from hydrogen, halogen, hydrocarbyl, substituted hydrocarbyl, heterohydrocarbyl, substituted heterohydrocarbyl or $SiR'_3$ where each R' is independently selected from hydrogen, halogen, hydrocarbyl, substituted hydrocarbyl, heterohydrocarbyl and substituted heterohydrocarbyl; and $R^5$ and $R^7$ are each as defined above.

Preferably $Y^1$ is C. Preferably $A^1$ to $A^3$ are each independently CR where each R is as defined above. In alternative preferred embodiments, $A^1$ and $A^3$ are both N and $A^2$ is CR, or one of $A^1$ to $A^3$ is N and the others are independently CR. Examples of such embodiments include the following:

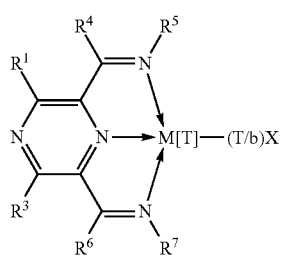

Formula (IVa)

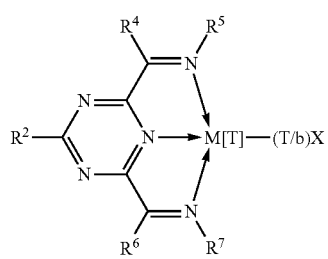

Formula (IVb)

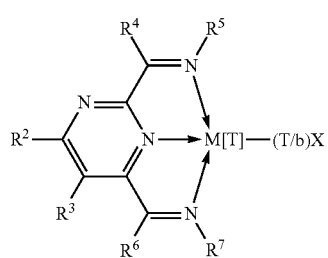

Formula (IVc)

wherein $R^1$, $R^2$ and $R^3$ are each independently H, or $C_1$-$C_{10}$ alkyl, aryl or aralkyl. Generally in the above Formulae, $R^5$ and $R^7$ are preferably independently selected from substituted or unsubstituted alicyclic, heterocyclic or aromatic groups, for example, phenyl, 1-naphthyl, 2-naphthyl, 2-methylphenyl, 2-ethylphenyl, 2,6-diisopropylphenyl, 2,3-diisopropylphenyl, 2,4-diisopropylphenyl, 2,6-di-n-butylphenyl, 2,6-dimethylphenyl, 2,3-dimethylphenyl, 2,4-dimethylphenyl, 2-t-butylphenyl, 2,6-diphenylphenyl, 2,4,6-trimethylphenyl, 2,6-trifluoromethylphenyl, 4-bromo-2,6-dimethylphenyl, 3,5-dichloro2,6-diethylphenyl, and 2,6-bis(2,6-dimethylphenyl)phenyl, cyclohexyl, pyrolyl, 2,5 dimethylpyrolyl and pyridinyl.

In a preferred embodiment $R^5$ is represented by the group "P" and $R^7$ is represented by the group "Q" as follows:

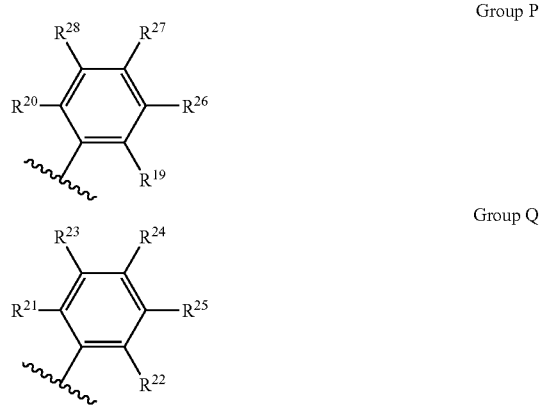

wherein $R^{19}$ to $R^{28}$ are independently selected from hydrogen, halogen, hydrocarbyl, substituted hydrocarbyl, heterohydrocarbyl or substituted heterohydrocarbyl; when any two or more of $R^1$ to $R^4$, $R^6$ and $R^{19}$ to $R^{28}$ are hydrocarbyl, substituted hydrocarbyl, heterohydrocarbyl or substituted heterohydrocarbyl, said two or more can be linked to form one or more cyclic substituents.

Preferably at least one of $R^{19}$, $R^{20}$, $R^{21}$ and $R^{22}$ is hydrocarbyl, substituted hydrocarbyl, heterohydrocarbyl or substituted heterohydrocarbyl. More preferably at least one of $R^{19}$ and $R^{20}$, and at least one of $R^{21}$ and $R^{22}$, is hydrocarbyl, substituted hydrocarbyl, heterohydrocarbyl or substituted heterohydrocarbyl. Most preferably $R^{19}$, $R^{20}$, $R^{21}$ and $R^{22}$ are all independently selected from hydrocarbyl, substituted hydrocarbyl, heterohydrocarbyl or substituted heterohydrocarbyl. $R^{19}$, $R_{20}$, $R^{21}$ and $R^{22}$ are preferably independently selected from methyl, ethyl, n-propyl, iso-propyl, n-butyl, sec-butyl, tert.-butyl, n-pentyl, neopentyl, n-hexyl, 4-methylpentyl, n-octyl, phenyl and benzy.

$R^1$, $R^2$, $R^3$, $R^4$, $R^6$, $R^{19}$, $R^{20}$, $R^{21}$, $R^{22}$, $R^{23}$, $R^{25}$, $R^{26}$ and $R^{28}$ are preferably independently selected from hydrogen and $C_1$ to $C_8$ hydrocarbyl, for example, methyl, ethyl, n-propyl, n-butyl, t-butyl, n-hexyl, n-octyl, phenyl and benzyl.

A particularly preferred complex has the Formula Z

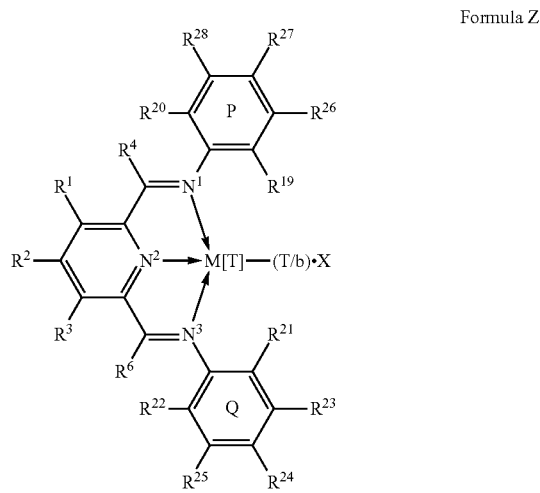

wherein all the substituents are as defined above. Preferred complexes are 2,6-diacetylpyridinebis(2,4,6 trimethyl anil) FeCl$_2$ and 2,6-diacetylpyridinebis(2,6 diisopropyl anil) FeCl$_2$.

In an alternative embodiment, applicable to all the above structures, R$^5$ is a group having the formula —NR$^{29}$R$^{30}$ and R$^7$ is a group having the formula —NR$^{31}$R$^{32}$, wherein R$^{29}$ to R$^{32}$ are independently selected from hydrogen, halogen, hydrocarbyl, substituted hydrocarbyl, heterohydrocarbyl or substituted heterohydrocarbyl, and may be linked to form one or more cyclic substituents. Examples of such compounds are disclosed in WO 00/50470.

Another preferred substituent for both R$^5$ and R$^7$ are pyrazolyl groups, as described in our own co-pending application PCT 02/02247.

Particularly preferred is the substituent having the formula (II):

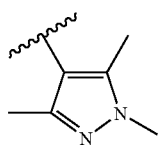

Formula (II)

The atom or group represented by X in the complexes disclosed above can be, for example, selected from halide, sulphate, nitrate, thiolate, thiocarboxylate, BF$_4^-$, PF$_6^-$, hydride, hydrocarbyloxide, carboxylate, hydrocarbyl, substituted hydrocarbyl and heterohydrocarbyl, or β-diketonates. Examples of such atoms or groups are chloride, bromide, methyl, ethyl, propyl, butyl, octyl, decyl, phenyl, benzyl, methoxide, ethoxide, isopropoxide, tosylate, triflate, formate, acetate, phenoxide and benzoate. Preferred examples of the atom or group X in the compounds of Formula (I) are halide, for example, chloride, bromide; hydride; hydrocarbyloxide, for example, methoxide, ethoxide, isopropoxide, phenoxide; carboxylate, for example, formate, acetate, benzoate; hydrocarbyl, for example, methyl, ethyl, propyl, butyl, octyl, decyl, phenyl, benzyl; substituted hydrocarbyl; heterohydrocarbyl; tosylate; and triflate. Preferably X is selected from halide, hydride and hydrocarbyl. Chloride is particularly preferred.

L may be for example an ether such as tetrahydrofuran or diethylether, an alcohol such as ethanol or butanol, a primary, secondary or tertiary amine, or a phosphine.

The chain growth catalyst system optionally employs a suitable activator. The activator compound for the catalyst of the present invention is suitably selected from organoaluminium compounds and hydrocarbylboron compounds, and can comprise more than one of these compounds. Suitable organoaluminium compounds include trialkyaluminium compounds, for example, trimethylaluminium, triethylaluminium, tributylaluminium, tri-n-octylaluminium, ethylaluminium dichloride, diethylaluminium chloride and alumoxanes. Alumoxanes are well known in the art as typically the oligomeric compounds which can be prepared by the controlled addition of water to an alkylaluminium compound, for example trimethylaluminium. Such compounds can be linear, cyclic or mixtures thereof. Commercially available alumoxanes are generally believed to be mixtures of linear and cyclic compounds. The cyclic alumoxanes can be represented by the formula [R$^{16}$AlO]$_s$ and the linear alumoxanes by the formula R$^{17}$(R$^{18}$AlO)$_s$ wherein s is a number from about 2 to 50, and wherein R$^{16}$, R$^{17}$, and R$^{18}$ represent hydrocarbyl groups, preferably C$_1$ to C$_6$ alkyl groups, for example methyl, ethyl or butyl groups. Another suitable type of organoaluminium compound is tris(pentafluorophenyl)aluminium.

Examples of suitable hydrocarbylboron compounds are dimethylphenylammoniumtetra(phenyl)borate, trityltetra(phenyl)borate, triphenylboron, dimethylphenylammonium tetra(pentafluorophenyl)borate, sodium tetrakis[(bis-3,5-trifluoromethyl)phenyl]borate, H$^+$(OEt$_2$)[(bis-3,5-trifluoromethyl)phenyl]borate, trityltetra(pentafluorophenyl)borate and tris(pentafluorophenyl)boron.

It is generally found that the quantity employed is sufficient to provide 0.1 to 20,000 atoms, preferably 1 to 2000 atoms of aluminium or boron per transition metal atom of the transition metal complex.

The complexes utilised in the present invention can if desired comprise more than one of the above-mentioned group 3-10 transition metal, group 3 main group metal, lanthanide or actinide complexes. The catalyst may comprise, for example a mixture of 2,6-diacetylpyridinebis(2,6-diisopropylanil)FeCl$_2$ complex and 2,6-diacetylpyridinebis(2,4,6-trimethylanil)FeCl$_2$ complex, or a mixture of 2,6-diacetylpyridine(2,6-diisopropylanil)CoCl$_2$ and 2,6-diacetylpyridinebis(2,4,6-trimethylanil)FeCl$_2$, In addition to said one or more defined transition metal compounds, the catalysts of the present invention can also include one or more other types of transition metal compounds or catalysts.

The complexes of the present invention can be unsupported or supported on a support material, for example, silica, silica/alumina, magnesium chloride, zeolites, alumina or zirconia, or on a polymer or prepolymer, for example polyethylene, polystyrene, or poly(aminostyrene), or on another heterogeneous catalyst. In another embodiment, both the complexes and activators are co-supported on the support material, polymer or prepolymer.

The chain growth reaction illustrated in equation 3 may utilize a neat zinc alkyl medium or may utilize a hydrocarbon solvent diluent such as toluene or heptane. When the chain is being grown by ethylene, higher (C$_3$-C$_{20}$+ alpha-olefins such as 1-octene may be used as a solvent or co-solvent. Reaction temperatures may vary from approximately room temperature 20° C. to 150° C. Pressures of ethylene may be varied from about 15 psig to about 1500 psig.

The mole ratio of transition metal to zinc alkyl may be varied from about $1\times10^{-7}$ to $1\times10^{-1}$ and preferably from about $1\times10^{-6}$ to $1\times10^{-2}$, and more preferably is in the range $2\times10^{-6}$ to $5\times10^{-3}$.

When conducting the chain growth reaction with some catalysts, it is helpful to activate the catalyst in order to avoid an induction period. One convenient method is to incubate the catalyst in aluminoxane solution in a separate vessel for about 5 minutes at 20° C. Subsequent addition to the zinc alkyl permits immediate uptake of ethylene.

As demonstrated by the examples below C$_2$ to C$_{20}$+ alpha-olefins can be recovered from alkylzinc compounds by catalytic displacement with, for example, a Ni catalyst, using ethylene and/or other alpha olefins as the displacing olefin. Alternatively, the chain growth products can be oxidized to zinc alkyl peroxide intermediates, oxidized and hydrolyzed using known procedures to produce linear primary alcohols, or used in known procedures to make other specialty materials.

BRIEF DESCRIPTION OF THE DRAWINGS

These and other aspects of the present invention will now be described, by way of example.

Figure 1:
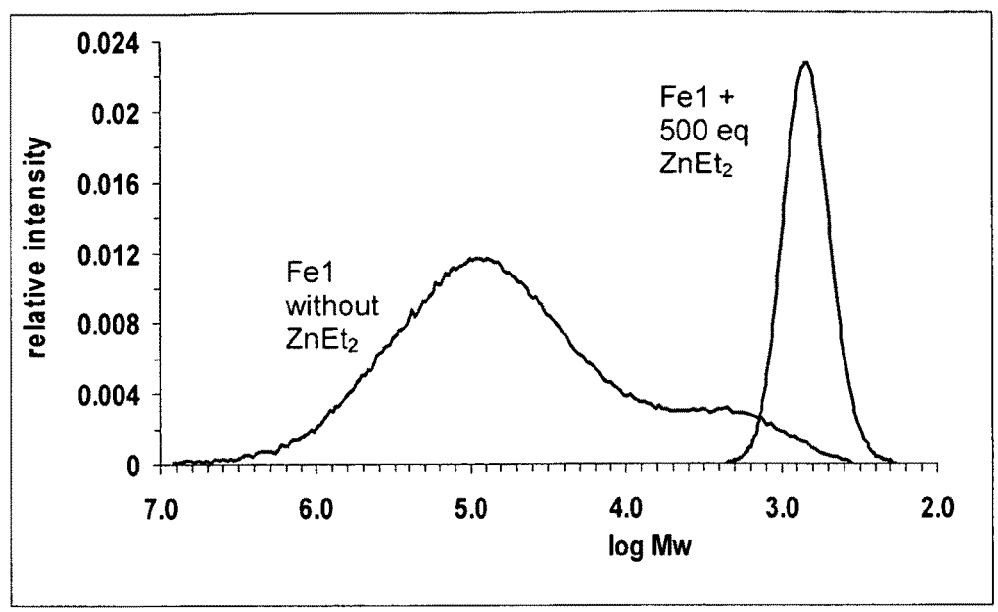
FIG. 1 is a graph showing the GPC of polyethylene produced in accordance with the process of the invention in the presence of diethylzinc and in the absence of diethylzinc.

The invention is further illustrated by, but is not intended to be limited to, the following general procedures and examples.

EXAMPLES

Manipulation of complexes, zinc alkyls, and optional activators, as well as the assembly and disassembly of reactors were conducted under a nitrogen atmosphere. Ethylene was polymer grade, used without purification. 2,6-bis[1-(2,6-diisopropylphenyl)imino)ethyl]pyridine iron(II) chloride and 2,6-bis[1-(2,6-diisopropylphenyl)imino)ethyl]pyridine cobalt(II) chloride were prepared according to the established procedure described in WO 99/12981. 2,4-bis[(2,6-diisopropylphenylimino)benzyl]-6-methylpyrimidine iron(II) chloride was prepared according to the procedure disclosed in GB 0100249. The complex used in Example 14 was prepared according to the procedure in WO 00/50470. The complex used in Example 15 was prepared according to the procedure of GB 0112023. Bis[N-(3-tert-butylsalicylidene)aniline]zirconium(IV) dichloride was prepared according to the procedure described in J. Am. Chem. Soc. 2001, 123, 6847-6856. Bis[N-(3-tert-butylsalicylidene)aniline]hafnium(IV) dichloride was prepared according to the procedure described in Macromol. Rapid Commun. 2002, 23, 1118-1123. [N-(3-(9-triptycenyl)salicylidene)-(8-aminoquinoline)]chromium(III) dichloride was prepared according to the procedure described in Chem. Commun. 2002, 1038-1039.

Bis(n-butylcyclopentadienyl)zirconium dichloride and [1,4-bis(2,6-diisopropylphenyl)-1,4-diaza-2,3-dimethylbutadiene]nickel(II) bromide were prepared according to the established literature procedures. MAO (10 wt % in toluene) was obtained from Witco. Bis(cyclopentadienyl)zirconium dichloride, bis(pentamethylcyclopentadienyl)zirconium dichloride, nickel(II) acetylacetonate, trimethyl aluminium (2M in toluene), dodecane (anhydrous), cyclohexane (anhydrous), and nonane (anhydrous) were obtained from Aldrich. Undecane was obtained from Aldrich and distilled over $CaH_2$ prior to use. Diethyl zinc solution was obtained from Acros (0.87M in toluene) or Aldrich (1.1M in toluene or heptane). rac-Ethylenebis(indenyl)zirconium(IV) dichloride and nickel naphthenate was obtained from Strem Chemical. 1-hexene (98.07% pure) from BP was used.

Example A

Synthesis of dihexylzinc n-Hexylmagnesiumchloride was prepared by addition of a solution of 1-chlorohexane (13 g, 108 mmol, filtered through neutral active alumina) in 50 ml diethylether to 3.2 g Mg in 40 ml diethylether over a period of 30 min. The mixture was allowed to reflux for an additional 2 h. The solution was transferred to 53 ml of a 1.0 M solution of $ZnCl_2$ (53 mmol) in diethylether over a period of 30 min and the reaction mixture was stirred overnight. The mixture was filtered and the remaining salts were washed twice with 100 ml diethylether. The combined filtrates were concentrated by removal of the solvent in vacuo. Vacuum distillation (0.08 mbar, 68° C.) gave dihexylzinc as a colourless liquid in a 63% yield (7.83 g, 33.2 mmol). $^1$H NMR (250 MHz, $C_6D_6$, 298 K): δ 1.57 (br quintet, 2H, Zn—$CH_2$—$CH_2$—, $^3$J=7 Hz), 1.36-1.28 (m, 6H, —$CH_2$—$CH_2$—$CH_2$—$CH_3$), 0.93 (br t, 3H, —$CH_3$, $^3$J=7 Hz), 0.29 (t, 2H, Zn—$CH_2$—, $^3$J=7 Hz) $^{13}$C NMR (62.9 MHz, $C_6D_6$, 298 K): δ 36.6, 32.3, 26.7, 23.1, 16.3, 14.4.

Example 1

Catalysed Chain Growth Using an Iron pyridylbisimine Catalyst

A) Preparation of Catalyst Solution

In a Schlenk flask was placed 2,6-bis[1-((2,6-diisopropylphenyl)imino)ethyl]pyridine iron(II) chloride (31 mg; 0.050 mmol) and 24 ml toluene. To the colourless solution was added MAO (3.0 ml), giving a clear orange solution that was stirred for 5 minutes at room temperature.

B) Chain Growth Reaction

In a 500 ml Schlenk flask was placed toluene (50 ml) and diethylzinc (2.5 ml of a 0.87M solution in hexane). The Schlenk flask with suba seal was evacuated and back-filled with ethylene (0.75 bar overpressure). Into this mixture was injected 2.5 ml of the catalyst solution prepared under A (containing 5.0 µmol Fe) giving a pale yellow solution. The reaction was run at room temperature for 30 minutes, whereby an exothermic reaction occurred within 1 minute. After 15 minutes the reaction mixture became viscous and cloudy and the temperature dropped. The reaction was stopped after 30 minutes by hydrolysis with 50 ml dilute HCl solution (2M). The precipitated polymer was filtered, washed with acetone, dried overnight in a vacuum oven (60° C.) and analysed by GPC and $^1$H-NMR. The organic fraction of the filtrate was separated, dried with $MgSO_4$ and filtered. The alkane content of this organic fraction was determined by gas chromatography using 2,2,4,4,6,8,8-heptamethylnonane as an internal reference. The GPC-trace of the toluene-insoluble fraction ($M_N$=600, $M_W$=700, PDI=1.1, activity=1000 g/mmol·h·bar) is shown in FIG. 1 together with the GPC for polyethylene produced under similar conditions but in the absence of diethylzinc ($M_N$=10000, $M_W$=192000, PDI=19.2, activity=1200 g/mmol·h·bar). $^1$H-NMR analysis of the product formed in the presence of diethylzinc shows the product to be fully saturated (43.6 methyl and 0.2 vinyl end-groups per 1000 C). GC-analysis of the toluene-soluble fraction confirmed the presence of even-numbered alkanes.

Example 2

The Effect of an Increase in the Diethylzinc-Concentration on Catalysed Chain Growth Using an Iron pyridylbisimine Catalyst In experiments similar to that described in Example 1, the effect of diethylzinc-concentration on the catalysed chain growth was studied (1 μmol Fe complex used in Example 1, 100 eq MAO, 1 bar ethylene, 50 ml toluene, 30 min, RT).

Figure 2:
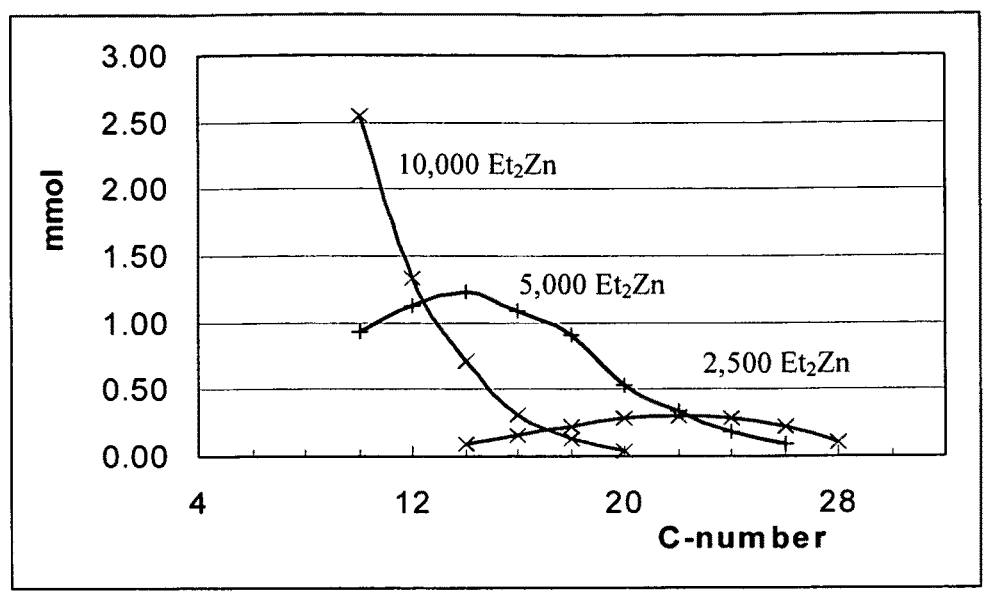
FIG. 2 is a graph showing the distribution of even alkanes at different diethylzinc concentrations.

The distribution of even alkanes (determined by GC) in the toluene-solutions produced with 2200 eq diethylzinc (activity=2800 g/mmol·h·bar), 4400 eq diethylzinc (activity=3000 g/mmol·h·bar) and 8700 eq diethylzinc (activity=2000 g/mmol·h·bar) are shown in FIG. 2.

Example 3

Time-Dependent Catalysed Chain Growth Using an Iron pyridylbisimine Catalyst A) Preparation of Catalyst Solution In a Schlenk flask was placed Fe complex used in Example 1 (12 mg; 0.020 mmol) and 24 ml toluene. To the colourless solution was added MAO (1.2 ml), giving a clear orange solution that was stirred for 5 minutes at room temperature.

B) Chain Growth Reaction

In a 250 ml jacketed two-necked roundbottom flask was placed toluene (50 ml), 0.40 ml distilled undecane and diethylzinc (4.0 ml of a 0.87M solution in hexane).

Figure 3:
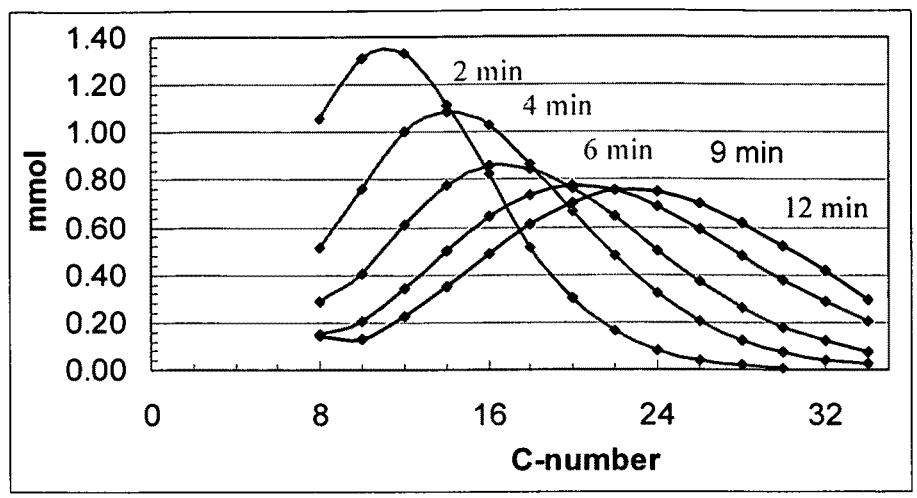
FIG. 3 is a graph showing yields of even alkanes at different reaction times.

The flask was equipped with suba seals, a thermometer and water cooling and was evacuated and back-filled with ethylene (0.75 bar overpressure). Into the solution was injected 2.5 ml of the catalyst solution prepared under A (containing 2.0 μmol Fe) giving a pale yellow solution. Within 30 seconds after injecting the catalyst the temperature rose from 19° C. to 32° C. where after the temperature dropped. The reaction was monitored by taking samples (~2 ml) from the reaction mixture through a cannula. The samples were hydrolysed with 2 ml dilute HCl solution (2M) and the alkane content of the toluene fraction was determined by GC using undecane as an internal reference. After 8 minutes the reaction mixture became viscous and cloudy. The reaction was stopped after 20 minutes by hydrolysis with 50 ml dilute HCl solution (2M). GC analysis of the samples 1-7 shows even alkanes with a Poisson distribution (Table 1 below and FIG. 3).

TABLE 1

Yields (in mg) of different alkanes (C8-C34) for samples 1-7

| Sample | C8 | C10 | C12 | C14 | C16 | C18 | C20 |
|---|---|---|---|---|---|---|---|
| 1 (2 min.) | 120.2 | 186.4 | 226.1 | 219.5 | 186.6 | 130.5 | 85.5 |
| 2 (4 min.) | 58.7 | 108.0 | 170.0 | 215.2 | 232.1 | 220.1 | 188.7 |
| 3 (6 min.) | 32.9 | 57.4 | 104.3 | 154.0 | 193.9 | 214.8 | 215.5 |
| 4 (9 min.) | 17.4 | 28.9 | 58.6 | 99.6 | 145.6 | 187.4 | 218.1 |
| 5 (12 min.) | 16.6 | 18.5 | 38.5 | 69.7 | 110.1 | 154.7 | 198.1 |
| 6 (15 min.) | 9.8 | 15.3 | 31.8 | 58.8 | 95.5 | 137.4 | 179.3 |
| 7 (18 min.) | 14.8 | 13.4 | 27.5 | 51.1 | 84.2 | 123.8 | 166.0 |

| Sample | C22 | C24 | C26 | C28 | C30 | C32 | C34 |
|---|---|---|---|---|---|---|---|
| 1 (2 min.) | 50.9 | 28.4 | 15.3 | 7.8 | 4.0 | | |
| 2 (4 min.) | 148.8 | 108.3 | 74.4 | 48.7 | 30.7 | 19.1 | 11.6 |
| 3 (6 min.) | 199.8 | 170.4 | 136.3 | 103.8 | 75.8 | 54.1 | 37.7 |
| 4 (9 min.) | 234.4 | 232.6 | 215.7 | 189.5 | 159.3 | 129.6 | 99.7 |
| 5 (12 min.) | 233.7 | 253.8 | 255.2 | 242.4 | 220.2 | 189.4 | 141.3 |
| 6 (15 min.) | 213.7 | 232.9 | 233.2 | 220.1 | 199.0 | 172.6 | 132.6 |
| 7 (18 min.) | 203.3 | 225.9 | 229.7 | 219.4 | 200.0 | 173.7 | 133.8 |

Example 4

Catalysed Chain Growth Using a zirconocene

In experiments similar to that described in example 1, the effect of bis(pentamethylcyclopentadienyl)zirconium dichloride ($ZrCp*_2Cl_2$) on the chain growth reactions of diethylzinc was studied (5 μmol $ZrCp*_2Cl_2$, 100 eq MAO, 1 bar ethylene, 50 ml toluene, 30 min, RT).

Figure 4:
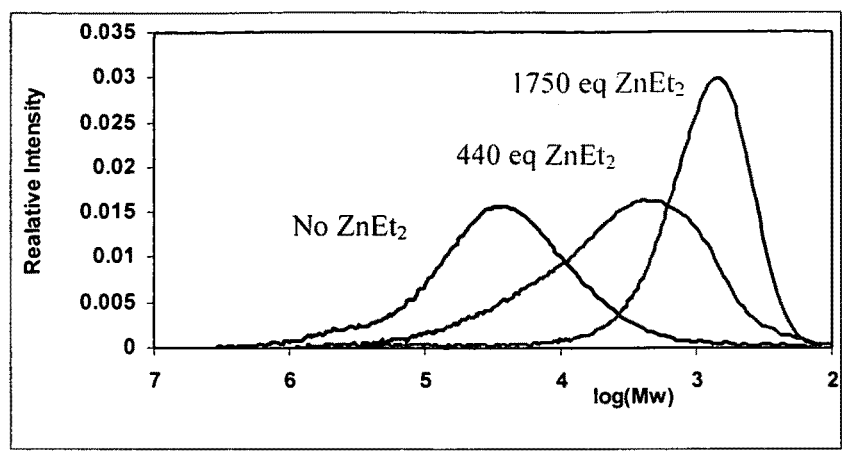
FIGS. 4 and 5 are graphs similar to the graph of FIG. 1.

The GPC-traces of the toluene-insoluble fractions produced with 440 eq diethylzinc ($M_N$=1600, $M_W$=12000, PDI=7.7, activity=3500 g/mmol·h·bar), 1750 eq diethylzinc ($M_N$=700, $M_W$=1500, PDI=2.2, activity=2600 g/mmol·h·bar) and in the absence of diethylzinc ($M_N$=9300, $M_W$=72000, PDI=7.7, activity=1200 g/mmol·h·bar) are shown in FIG. 4. $^1$H-NMR analysis shows the product formed in the presence of diethylzinc to be fully saturated (14.9 methyl and 0.2 vinyl end-groups per 1000 C for the reaction with 440 eq $ZnEt_2$ and 37.5 methyl and 0.1 vinyl end-groups per 1000 C for the reaction with 1750 eq $ZnEt_2$).

Example 5

Catalysed Chain Growth Using a metallocene Catalyst

In experiments similar to that described in Example 1, the effect of rac-ethylenebis(indenyl)zirconium(IV) dichloride (rac-(EBI)$ZrCl_2$) on the chain growth reactions of diethylzinc was studied (5 μmol rac-(EBI)$ZrCl_2$, 100 eq MAO, 1 bar ethylene, 50 ml toluene, 30 min, RT).

Figure 5:
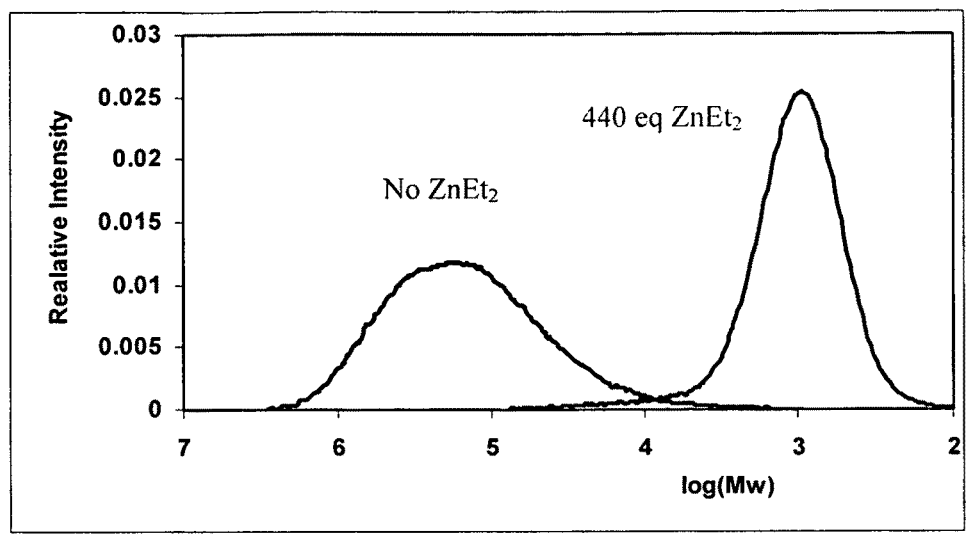

The GPC-traces of the toluene-insoluble fractions produced with 440 eq diethylzinc ($M_N$=800, $M_W$=1600, PDI=1.9, activity=2400 g/mmol·h·bar) and in the absence of diethylzinc ($M_N$=66000, $M_W$=261000, PDI=3.9, activity=1300 g/mmol·h·bar) are shown in FIG. 5. $^1$H-NMR analysis shows the product formed in the presence of diethylzinc to be fully saturated (31.9 methyl and 0.2 vinyl end-groups per 1000 C).

Example 6

Catalysed Chain Growth Using a Metallocene Catalyst

Figure 6:
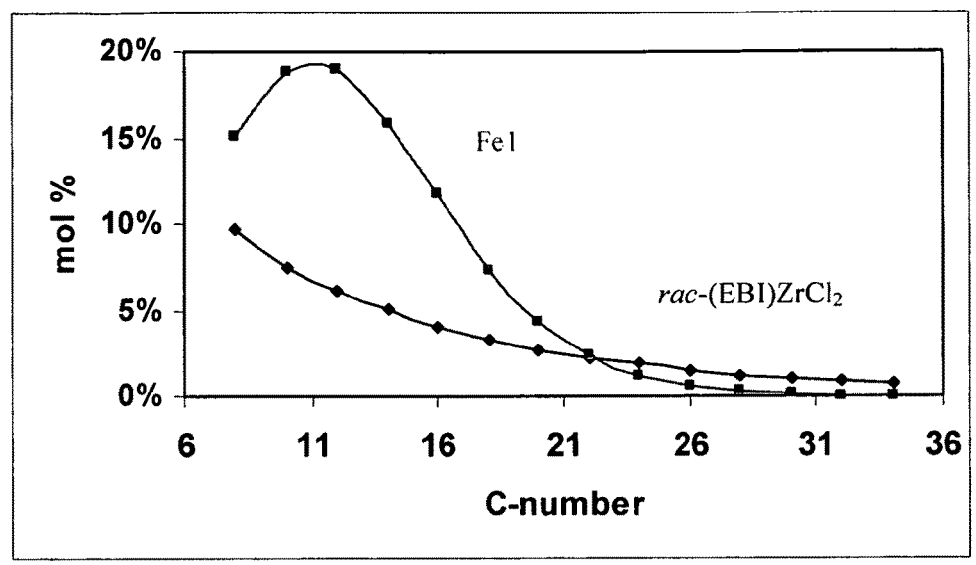
FIG. 6 is a graph showing the distribution of even alkanes.

In an experiment similar to that described in example 3 samples were taken from a reaction mixture containing (rac-(EBI)$ZrCl_2$) and diethylzinc (2 μmol rac-(EBI)$ZrCl_2$, 100 eq MAO, 2200 eq $ZnEt_2$, 1 bar ethylene, 50 ml toluene, RT). Only the first sample taken after 2.5 min resulted in toluene-soluble alkanes with a distribution shown in FIG. 6 together with the GC-trace from a comparable run with Fe1 (see example 3).

Example 7

Catalysed Chain Growth Using a Ni(α-diimine) Catalyst

In experiments similar to that described in Example 1, the effect of [1,4-bis(2,6-diisopropylphenyl)-1,4-diaza-2,3-dimethylbutadiene]nickel(II) bromide ((dab)NiBr$_2$) on the chain growth reactions of diethylzinc was studied (5 μmol (dab)NiBr$_2$, 100 eq MAO, 1 bar ethylene, 50 ml toluene, 1 h, RT).

Figure 7:
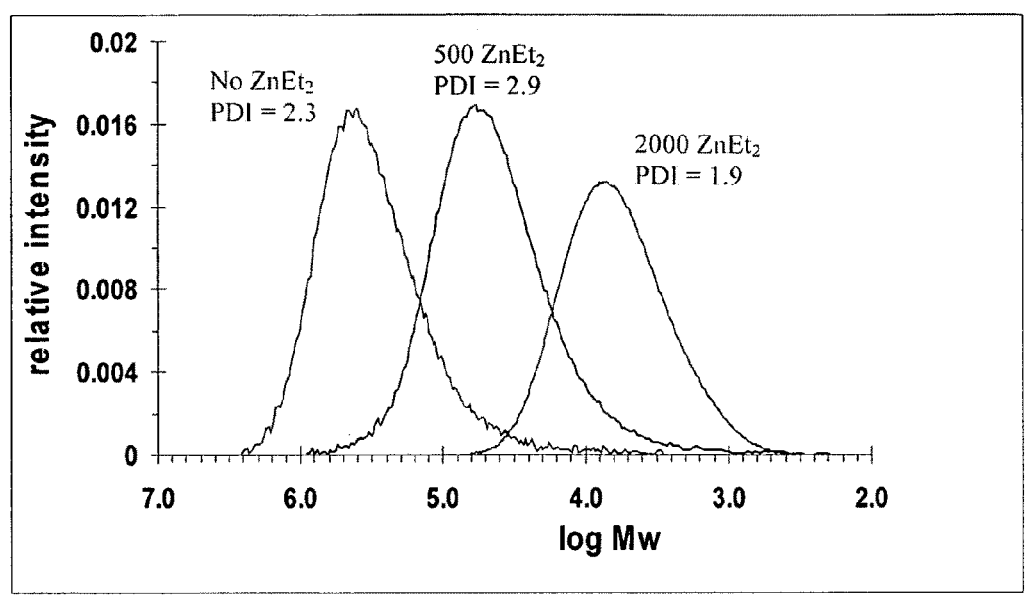
FIG. 7 is a graph similar to the graph of FIG. 1.
Figure 8:
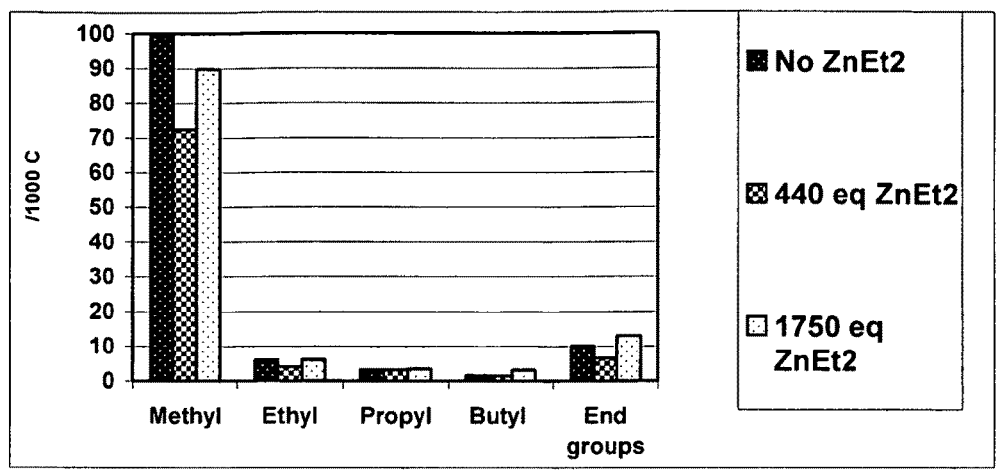
FIG. 8 is a graph showing that diethylzinc does not affect the branching level in the reaction.

The GPC-traces of the polymer produced with 440 eq diethylzinc (M$_N$=23000, M$_W$=67000, PDI=2.9, activity=250 g/mmol·h·bar), with 1750 eq diethylzinc (M$_N$=4300, M$_W$=8400, PDI=1.9, activity=300 g/mmol·h·bar) and in the absence of diethylzinc (M$_n$=193000, M$_w$=435000, PDI=2.3, activity=300 g/mmol·h·bar) are shown in FIG. 7. FIG. 8 shows that diethylzinc does not affect the branching level in these reactions.

Example 8

Catalysed Chain Growth Using an Iron pyrimidylbisimine Catalyst

Figure 9:
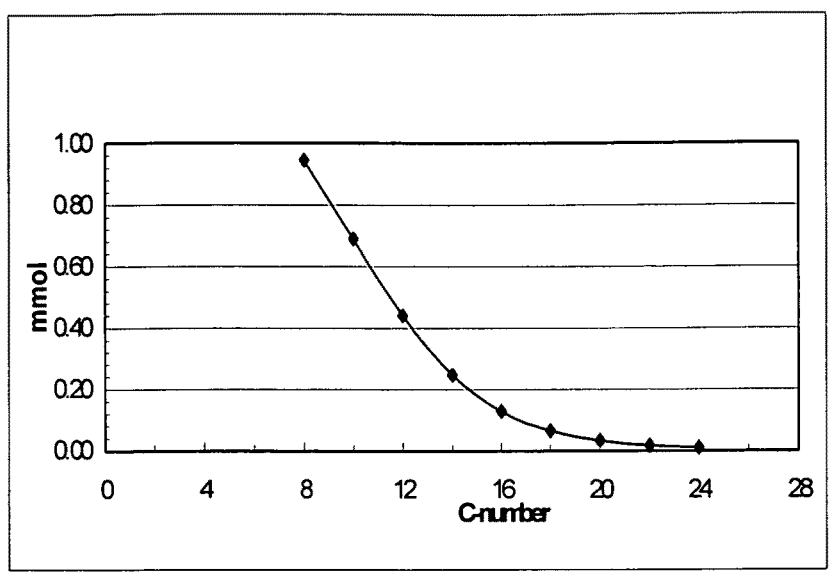
FIG. 9 is a graph similar to the graph of FIG. 6.

In experiments similar to that described in example 1, the effect of 2,4-bis[(2,6-diisopropylphenylimino)benzyl]-6-methylpyrimidine iron (II) chloride (N4Fe1) on the chain growth reactions of diethylzinc was studied (5 μmol N4Fe1, 100 eq MAO, 1 bar ethylene, 50 ml toluene, 30 min, RT). The product consisted of toluene-soluble, even alkanes (>95%) with the distribution shown in FIG. 9.

Example 9

Catalysed Chain Growth Using a Cobalt Pyridylbisimine Catalyst

Figure 10:
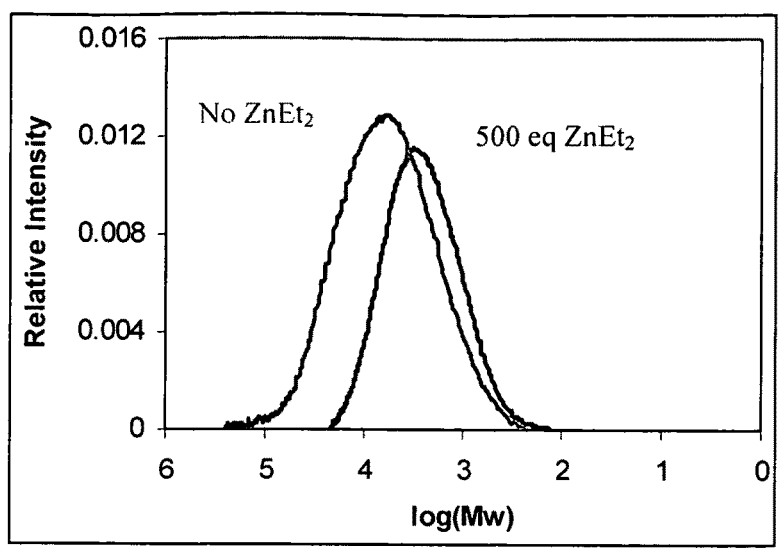
FIG. 10 is a graph similar to the graph of FIG. 1.

In experiments similar to that described in example 1, the effect of 2,6-bis[1-((2,6-diisopropylphenyl)imino)ethyl]pyridine cobalt(II) chloride on the chain growth reactions of diethylzinc was studied (5 μmol Co, 100 eq MAO, 1 bar ethylene, 50 ml toluene, 30 min, RT). The GPC-traces of the toluene-insoluble fractions produced with 500 eq diethylzinc (M$_N$=1800, M$_W$=3500, PDI=2.0, activity=600 g/mmol·h·bar) and in the absence of diethylzinc (M$_N$=3300, M$_W$=11000, PDI=3.2) are shown in FIG. 10. $^1$H-NMR and GC analysis show 85% of the product formed in the reaction with 500 eq diethylzinc to be fully saturated (11.3 methyl and 1.3 vinyl end-groups per 1000 C).

Example 10

Displacement of 1-hexene from dihexylzinc

Figure 11:
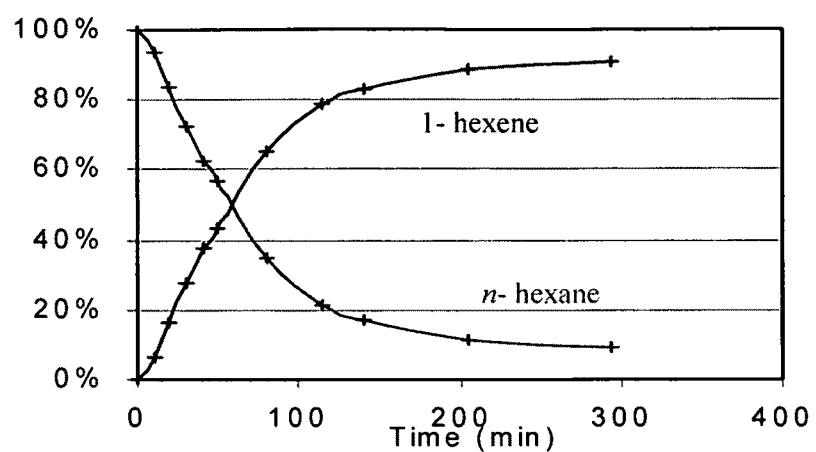
FIG. 11 is a graph showing the hexane versus 1-hexene content of the toluene fraction.

A 250 ml Schlenk flask with suba seal containing 645 mg dihexylzinc (2.74 mmol) and 40 ml toluene was evacuated and back-filled with ethylene (0.75 bar overpressure). A solution of 35.4 mg Ni(acac)$_2$ (0.138 mmol) in 3 ml toluene was injected into the solution. The reaction was followed with time by taking samples, hydrolysing them with 2M HCl and comparing the hexane versus 1-hexene content of the toluene fraction (determined by GC), as shown in FIG. 11.

Example 11

Figure 12:
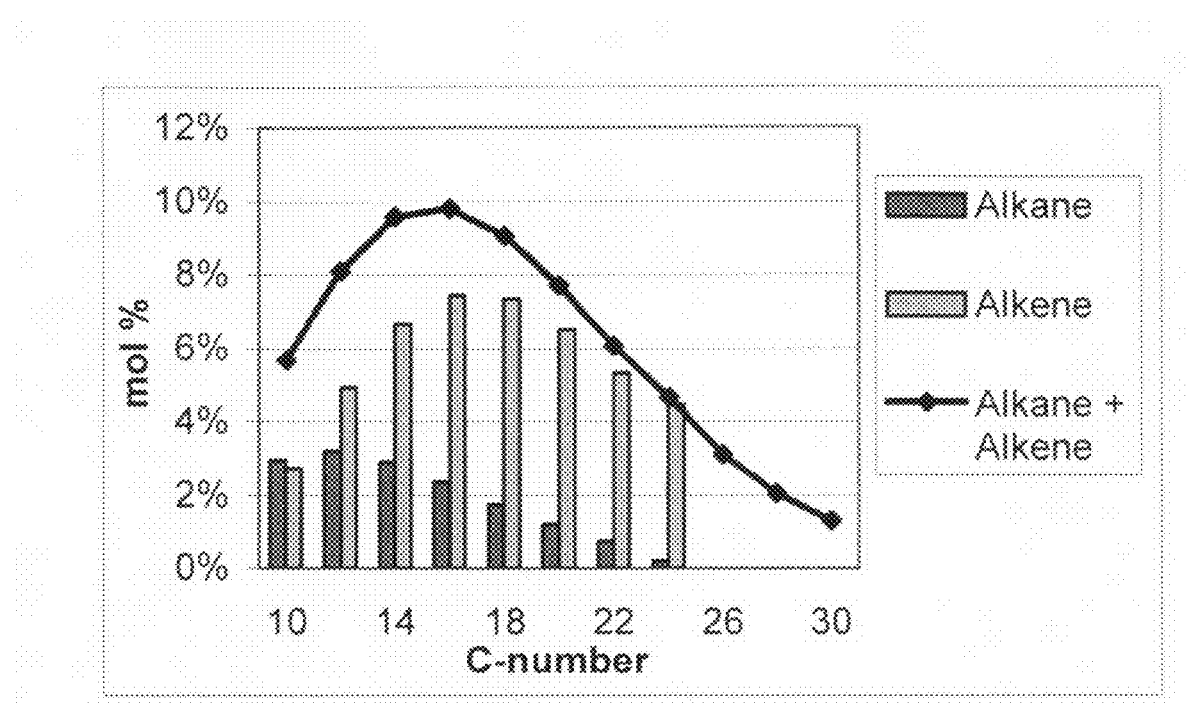
FIG. 12 is a graph showing the GC-analysis of the toluene solution.

Catalysed Chain Growth Followed by Chain Displacement of α-olefins from dialkylzinc A mixture of dialkylzinc was produced in a reaction similar to example 1 (2 μmol Fe1, 1750 eq ZnEt$_2$, 100 eq MAO, 1 bar ethylene, 50 ml toluene, 8 min, RT). After 8 min reaction the contents of the Schlenk flask were transferred into another Schlenk containing dry silica. After 15 min stirring the toluene solution was filtered into a Schlenk containing a solution of Ni(acac)$_2$ (0.35 mmol) in 10 ml toluene under 1 bar ethylene pressure. The reaction mixture was hydrolysed after 30 min by addition of 50 ml 2M HCl. GC-analysis of the toluene solution (FIG. 12) shows a distribution consisting of 75% even 1-alkenes and 25% even alkanes.

Example 12

Displacement of ethylene from diethylzinc by 1-hexene

A heavy-walled Fischer-Porter tube containing 8.0 mL diethylzinc, 1.0 mL nonane, and 15.5 mL 1-hexene was purged with ethylene (1 bar) three times, sampled (t$_0$), heated for 1.0 h at 60° C. under 100 psi ethylene, cooled to room temperature and sampled (t=60 min). Nickel naphthenate (0.66 mL of 1.26×10$^{-2}$ M in dodecane) solution was added to the solution in the F-P tube and allowed to stir for 1.0 h at room temperature, sampled (t=120 min), the gas volume above the solution was purged three times with nitrogen (1 bar), brought to 100 psi nitrogen, then heated at 60° C. for 1 h, and sampled (t=180 min). The samples were hydrolysed and hexene and hexane analysed by GC. The amount of hexane corresponds to the amount of hexyl-zinc moieties formed from the displacement of ethylene from the diethylzinc. The extent of displacement is provided in Table 2.

TABLE 2

| Hexene Displacement of Et—Zn Catalysed by 43 ppm Ni | |
|---|---|
| Total Time (minutes) | R—Zn Groups as Hexyl (%) |
| 0 | 0.00 |
| 60 | 0.41 |
| 120 | 15.14 |
| 180 | 31.49 |

Example 13

Catalysed Chain Growth Using a Metallocene Catalyst

Figure 13:
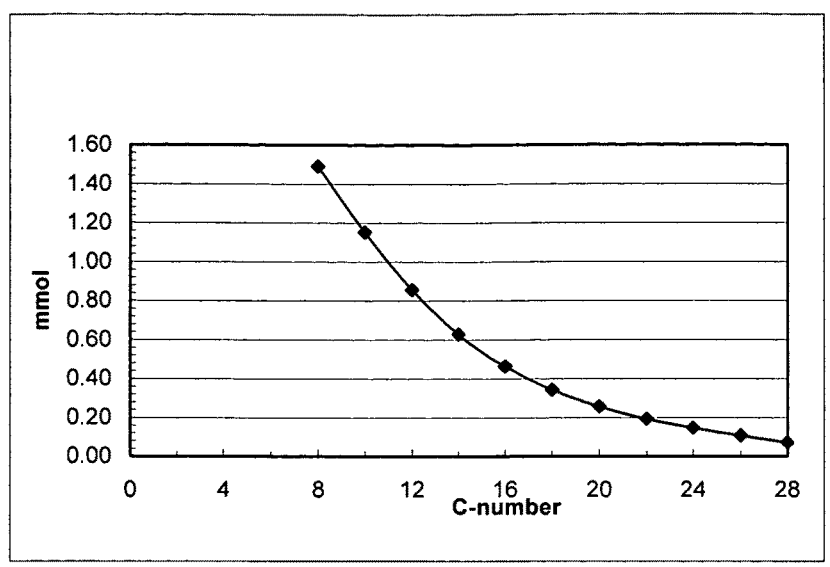
FIG. 13 is a graph similar to the graph of FIG. 6.

In experiments similar to that described in example 1, the effect of bis(n-butylcyclopentadienyl)zirconium dichloride (Zr(CpBu)$_2$Cl$_2$) on the chain growth reactions of diethylzinc was studied (5 μmol rac-(EBI)ZrCl$_2$, 2000 eq ZnEt$_2$ 100 eq MAO, 1 bar ethylene, 50 ml toluene, 30 min, RT). The product consisted of toluene-soluble, even alkanes (>95%) with the distribution shown in FIG. 13.

Example 14

Catalysed Chain Growth Using an Iron Pyridylbisimine Catalyst

In experiments similar to that described in example 1, the effect of the iron pyridyl bisimine complex below on the chain growth reactions of diethylzinc was studied (5 µmol Fe, 2000 eq ZnEt₂ 100 eq MAO, 1 bar ethylene, 50 ml toluene, 30 min, RT). GC-analysis of the toluene-soluble fraction shows a series of oligomers of which 75% is even alkanes and 25% is even alkenes.

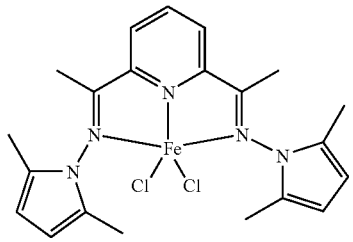

Example 15

Catalysed Chain Growth Using an Iron Pyridylbisimine Catalyst

In experiments similar to that described in example 1, the effect of the iron pyridyl bisimine complex below on the chain growth reactions of diethylzinc was studied (5 µmol Fe, 2000 eq ZnEt₂ 100 eq MAO, 1 bar ethylene, 50 ml toluene, 30 min, RT). GC-analysis of the toluene-soluble fraction shows a series of oligomers of which 70% is even alkanes and 30% is even alkenes.

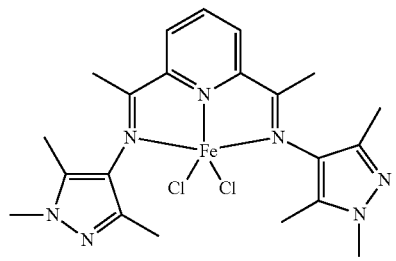

Example 16

Catalysed Chain Growth Using a Phenoxyimine Zircomium Catalyst

In experiments similar to that described in example 1, the effect of bis[N-(3-tert-butylsalicylidene)aniline]zirconium (IV) dichloride on the chain growth reactions of diethylzinc was studied (5 µmol Zr complex, 100 eq MAO, 1 bar ethylene, 50 ml toluene, 30 min, RT).

Figure 14:
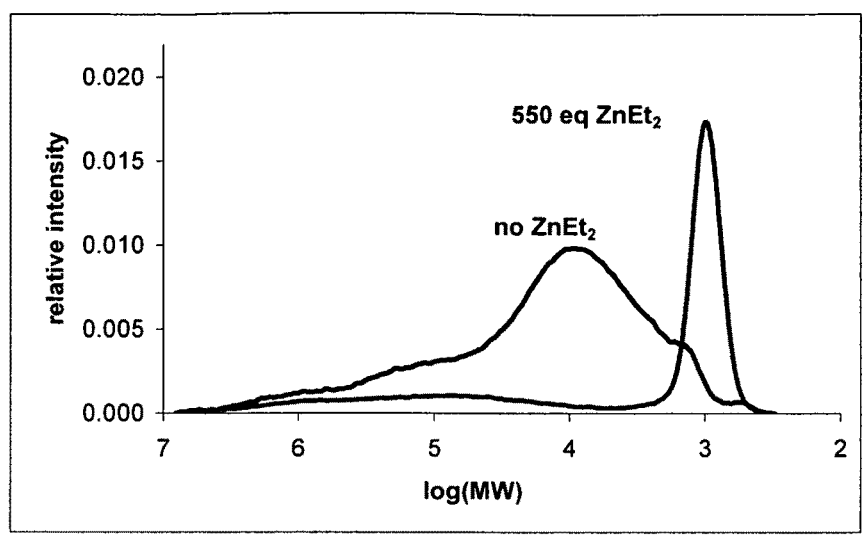
FIG. 14 is a graph showing the GPC of toluene insoluble fractions produced in accordance with the process of the invention in the presence of diethylzinc and in the absence of diethylzinc.

The GPC-trace of the toluene-insoluble fractions produced with 550 eq diethylzinc ($M_N$=1000, $M_W$=1100, PDI=1.1, activity=1700 g/mmol·h·bar) and in the absence of diethylzinc ($M_N$=5500, $M_W$=128000, PDI=23, activity=1600 g/mmol·h·bar) is shown in FIG. 14. ¹H-NMR analysis shows the product formed in the presence of diethylzinc to be fully saturated (33.6 methyl and 0.5 vinyl end-groups per 1000 C).

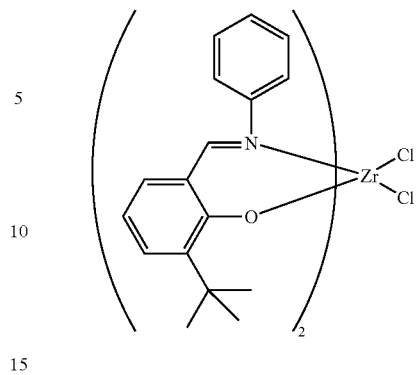

Example 17

Catalysed Chain Growth Using a Phenoxyimine Hafnium Catalyst

In experiments similar to that described in example 1, the effect of bis[N-(3-tert-butylsalicylidene)aniline]hafnium (IV) dichloride on the chain growth reactions of diethylzinc was studied (5 µmol Hf complex, 100 eq MAO, 1 bar ethylene, 50 ml toluene, 30 min, RT).

Figure 15:
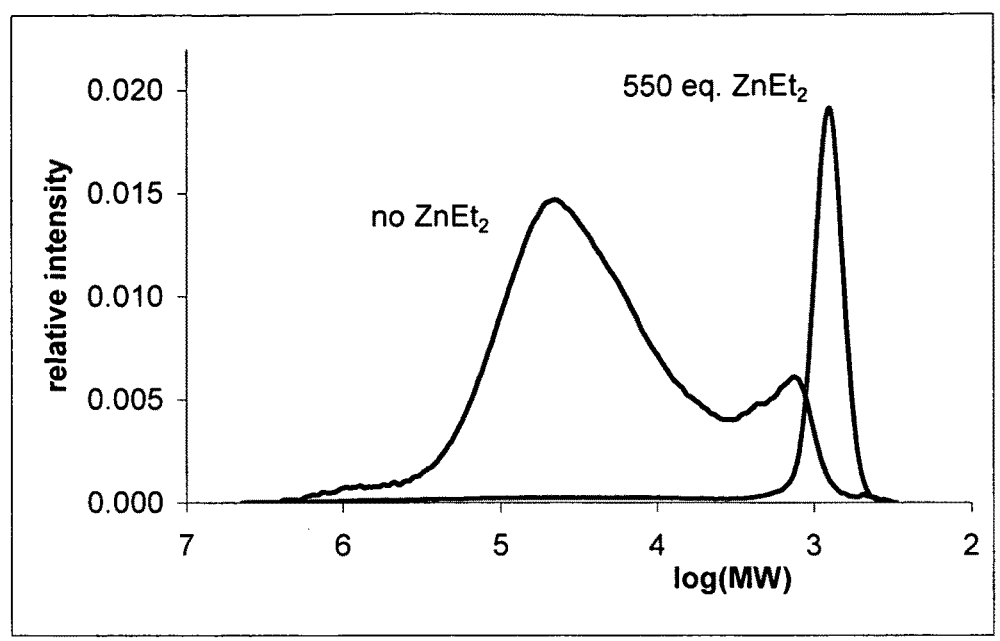
FIG. 15 is a graph similar to the graph of FIG. 14.

The GPC-trace of the toluene-insoluble fractions produced with 550 eq diethylzinc ($M_N$=800, $M_W$=900, PDI=1.1, activity=900 g/mmol·h·bar) and in the absence of diethylzinc ($M_N$=7000, $M_W$=65000, PDI=9.4, activity=800 g/mmol·h·bar) is shown in FIG. 15. ¹H-NMR analysis shows the product formed in the presence of diethylzinc to be fully saturated (51.3 methyl and 0.0 vinyl end-groups per 1000 C).

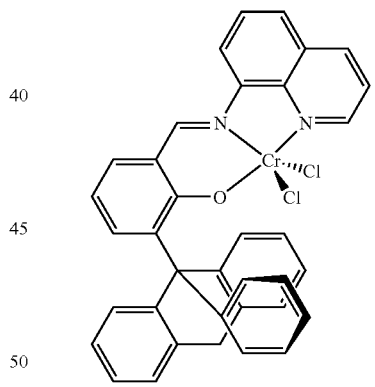

Example 18

Time-Dependent Catalysed Chain Growth Using Phenoxyimine Hafnium Catalyst

Figure 16:
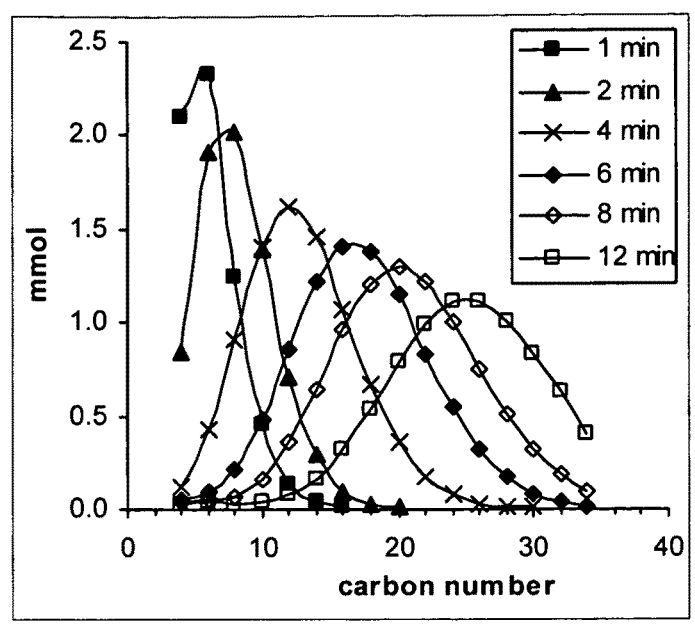
FIG. 16 is a graph showing the GPC of samples taken after 1, 2, 4, 6, 8, and 12 minutes.

In experiments similar to that described in example 2A and 2B, the time dependent catalysed chain growth effect of bis [N-(3-tert-butylsalicylidene)aniline]hafnium(IV) dichloride with diethylzinc was studied (2 µmol Hf complex, 500 eq MAO, 2200 eq ZnEt₂, 1 bar ethylene, 50 ml toluene, 30 min, RT). GC analysis of the samples taken after 1, 2, 4, 6, 8 and 12 minutes shows even alkanes with a Poisson distribution (FIG. 16).

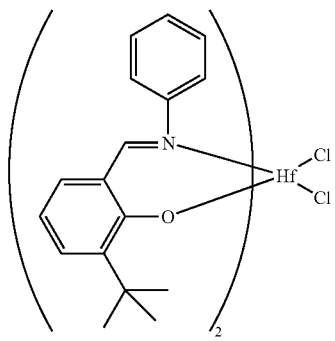

Example 19

Catalysed Chain Growth Using a Phenoxyimine Chromium Catalyst

In experiments similar to that described in example 1, the effect of [N-(3-(9-triptycenyl)salicylidene)-(8-aminoquinoline)]chromium(III) dichloride on the chain growth reactions of diethylzinc was studied (5 μmol Cr complex, 100 eq MAO, 1 bar ethylene, 50 ml toluene, 30 min, RT).

Figure 17:
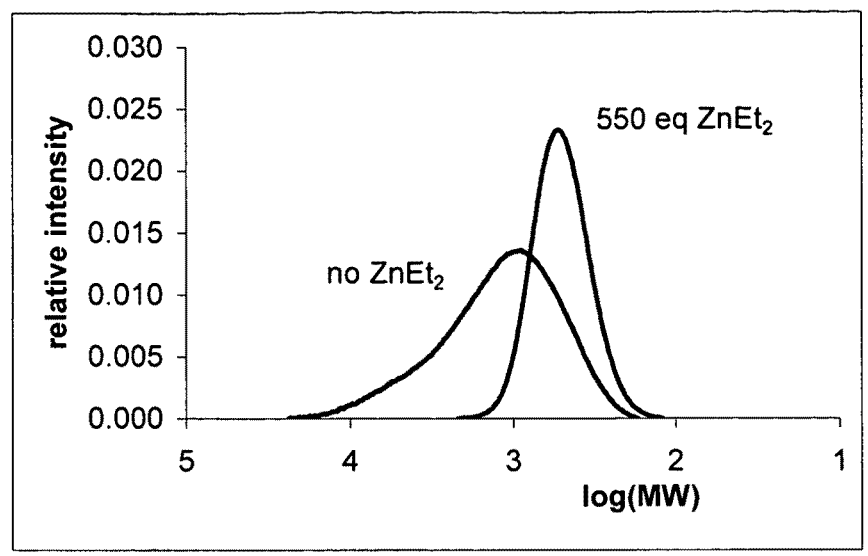
FIG. 17 is a graph similar to the graph of FIG. 15.

The GPC-trace of the toluene-insoluble fractions produced with 550 eq diethylzinc ($M_N$=500, $M_W$=600, PDI=1.2, activity=1400 g/mmol·h·bar) and in the absence of diethylzinc ($M_N$=900, $M_W$=1800, PDI=2.0, activity=1800 g/mmol·h·bar) is shown in FIG. 17. $^1$H-NMR analysis shows the product formed in the presence of diethylzinc to be mainly saturated (50.0 methyl and 7.5 vinyl end-groups per 1000 C).

Example 20

Time-Dependent Catalysed Chain Growth Using Phenoxyimine Chromium Catalyst

Figure 18:
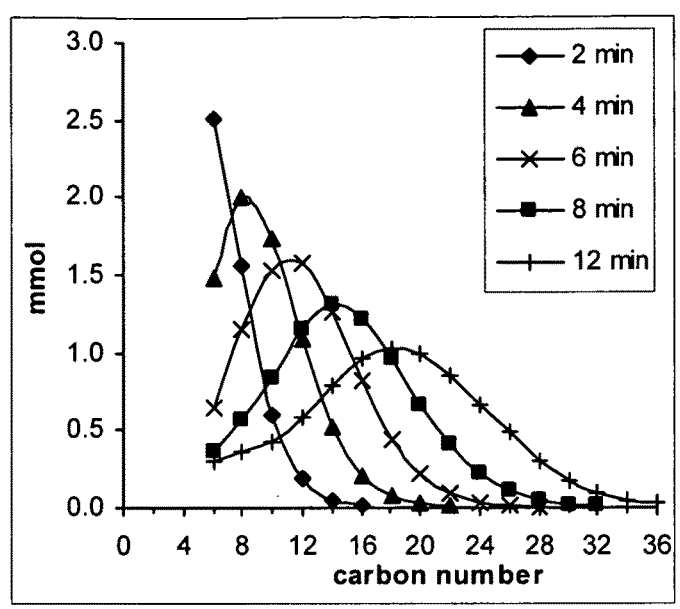
FIG. 18 is a graph similar to the graph of FIG. 16.

In experiments similar to that described in example 2A and 2B, the time dependent catalysed chain growth effect of [N-(3-(9-triptycenyl)salicylidene)-(8-aminoquinoline)]chromium(III) dichloride with diethylzinc was studied (2 μmol Cr complex, 100 eq MAO, 2200 eq ZnEt$_2$, 1 bar ethylene, 50 ml toluene, 30 min, RT). GC analysis of the samples taken after 2, 4, 6, 8 and 12 minutes shows even alkanes with a Poisson distribution (FIG. 18).

The invention claimed is:

1. A composition comprising:
i) a plurality of zinc alkyl compounds; and
ii) one or more chain growth catalysts;
at least one of the chain growth catalysts being selected from the group consisting of:
a) a complex of Formula (IV)

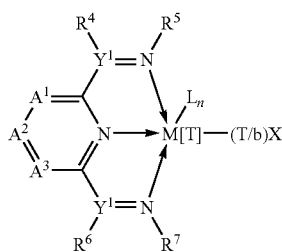

wherein M[T] is Ti[II], Ti[III], Ti[IV], Zr[II], Zr[III], Zr[IV], Hf[II], Hf[III], Hf[IV], V[II], V[III], V[IV], Nb[II], Nb[III], Nb[IV], Nb[V], Ta[II], Ta[III], Ta[IV], Cr[II], Cr[III], Mn[II], Mn[III], Mn[IV], Fe[II], Fe[III], Ru[II], Ru[III], Ru[IV], Co[II], Co[III], Rh[II], Rh[III], Ni[II], or Pd[II]; X represents an atom or group covalently or ionically bonded to the transition metal M; T is the oxidation state of the transition metal M and b is the valency of the atom or group X; $Y^1$ is C or P($R^c$), $A^1$ to $A^3$ are each independently N or P or CR, with the proviso that at least one is CR; and R, $R^c$, $R^4$, $R^5$, $R^6$ and $R^7$ are each independently selected from hydrogen, halogen, hydrocarbyl, substituted hydrocarbyl, heterohydrocarbyl, substituted heterohydrocarbyl or SiR'$_3$ where each R' is independently selected from hydrogen, halogen, hydrocarbyl, substituted hydrocarbyl, heterohydrocarbyl or substituted heterohydrocarbyl;

b) a complex of Formula (III)

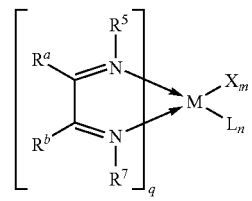

wherein M is Cr[II], Cr[III], Mn[II], Mn[III], Mn[IV], Fe[II], Fe[III], Ru[II], Ru[III], Ru[IV], Co[II], Co[III], Rh[II], Rh[III], Pd[II], Cu[I], or Cu[II]; X represents an atom or group covalently or ionically bonded to the transition metal M; $R^a$ and $R^b$ are each independently selected from hydrogen, halogen, hydrocarbyl, substituted hydrocarbyl, heterohydrocarbyl, substituted heterohydrocarbyl or SiR'$_3$ where each R' is independently selected from hydrogen, halogen, hydrocarbyl, substituted hydrocarbyl, heterohydrocarbyl or substituted heterohydrocarbyl, and $R^a$ and $R^b$ may be joined together to form a ring; $R^5$ and $R^7$ are each as defined above; and L is a group datively bound to M; n is from 0 to 5; m is 1 to 3 and q is 1 or 2;

c) a complex of Formula (II)

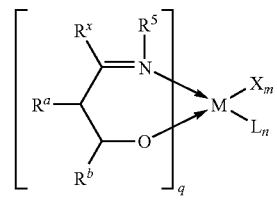

wherein M is Y[II], Y[III], Sc[II], Sc[III], Ti[II], Ti[III], Ti[IV], Zr[II], Zr[III], Zr[IV], Hf[II], Hf[III], Hf[IV], V[II], V[III], V[IV], Nb[II], Nb[III], Nb[IV], Nb[V], Ta[II], Ta[III], Ta[IV], Cr[II], Cr[III], Mn[II], Mn[III], Mn[IV], Fe[II], Fe[III], Ru[II], Ru[III], Ru[IV], Co[II], Co[III], Rh[II], Rh[III], Ni[II], or Pd[II], X represents an atom or group covalently or ionically bonded to the transition metal M; $R^a$, $R^b$, $R^x$, and $R^5$ are each independently selected from hydrogen, halogen, hydrocarbyl, substituted hydrocarbyl, heterohydrocarbyl, substituted heterohydrocarbyl or SiR'$_3$ where each R' is independently selected from hydrogen, halogen, hydrocarbyl, substituted hydrocarbyl, heterohydrocarbyl or substituted heterohydrocarbyl, and any adjacent ones may be joined together to form a ring; L is a group datively bound to M; n is from 0 to 5; m is 1 to 3 and q is 1 or 2; and d) a complex of Formula (I)

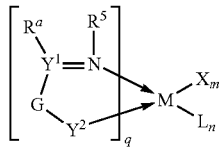

wherein M is Y[II], Y[III], Sc[II], Sc[III], Ti[II], Ti[III], Ti[IV], Zr[II], Zr[III], Zr[IV], Hf[II], Hf[III], Hf[IV], V[II], V[III], V[IV], Nb[II], Nb[III], Nb[IV], Nb[V], Ta[II], Ta[III], Ta[IV], Cr[II], Cr[III], Mn[II], Mn[III], Mn[IV], Fe[II], Fe[III], Ru[II], Ru[III], Ru[IV], Co[II], Co[III], Rh[II], Rh[III], Ni[II], or Pd[II], X represents an atom or group covalently or ionically bonded to the transition metal M; $Y^1$ is C or P($R^c$); $Y^2$ is —O($R^7$), —O (in which case the bond from O to M is covalent), —C($R^b$)=O, —C($R^b$)=N($R^7$), —P($R^b$)($R^d$)=N($R^7$) or —P($R^b$)($R^d$)=O; $R^a$, $R^b$, $R^c$, $R^d$, $R^5$ and $R^7$ are each independently selected from hydrogen, halogen, hydrocarbyl, substituted hydrocarbyl, heterohydrocarbyl, substituted heterohydrocarbyl or $SiR'_3$ where each R' is independently selected from hydrogen, halogen, hydrocarbyl, substituted hydrocarbyl, heterohydrocarbyl or substituted heterohydrocarbyl, and any adjacent ones may be joined together to form a ring; G is either a direct bond between $Y^1$ and $Y^2$, or is a bridging group, which optionally contains a third atom linked to M when q is 1; L is a group datively bound to M; n is from 0 to 5; m is 1 to 3 and q is 1 or 2.

2. The composition of claim 1 wherein the mole ratio of transition metal M to zinc alkyl is between $1 \times 10^{-7}$ and $1 \times 10^{-1}$.

3. The composition of claim 1 further comprising an activator.

4. The composition of claim 1 wherein the chain growth catalyst system comprises a complex of the Formula (IV):

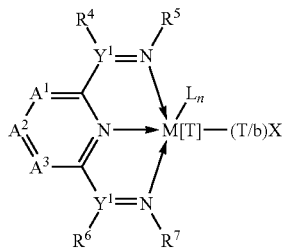

wherein M[T] is Ti[II], Ti[III], Ti[IV], Zr[II], Zr[III], Zr[IV], Hf[II], Hf[III], Hf[IV], V[II], V[III], V[IV], Nb[II], Nb[III], Nb[IV], Nb[V], Ta[II], Ta[III], Ta[IV], Cr[II], Cr[III], Mn[II], Mn[III], Mn[IV], Fe[II], Fe[III], Ru[II], Ru[III], Ru[IV], Co[II], Co[III], Rh[II], Rh[III], Ni[II], or Pd[II]; X represents an atom or group covalently or ionically bonded to the transition metal M; T is the oxidation state of the transition metal M and b is the valency of the atom or group X; $Y^1$ is C or P($R^c$), $A^1$ to $A^3$ are each independently N or P or CR, with the proviso that at least one is CR; and R, $R^c$, $R^4$, $R^5$, $R^6$ and $R^7$ are each independently selected from hydrogen, halogen, hydrocarbyl, substituted hydrocarbyl, heterohydrocarbyl, substituted heterohydrocarbyl or $SiR'_3$ where each R' is independently selected from hydrogen, halogen, hydrocarbyl, substituted hydrocarbyl, heterohydrocarbyl or substituted heterohydrocarbyl.

5. The composition according to claim 4 wherein $Y^1$ is C, and $A^1$ to $A^3$ are each independently CR, or $A^1$ and $A^3$ are both N and $A^2$ is CR, or one of $A^1$ to $A^3$ is N and the others are independently CR.

6. The composition according to claim 4 wherein $Y^1$ is C, $A^1$ to $A^3$ are each independently CR, and $R^5$ is represented by the group "P" and $R^7$ is represented by the group "Q" as follows:

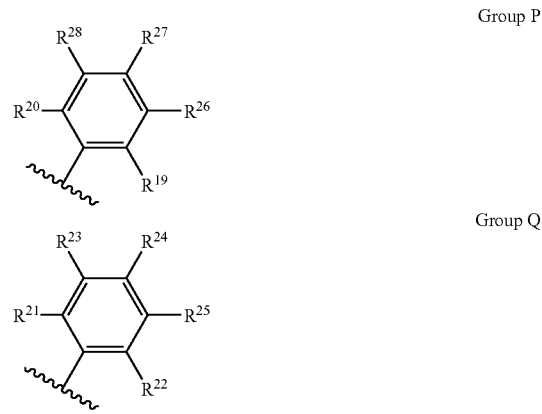

wherein $R^{19}$ to $R^{28}$ are independently selected from hydrogen, halogen, hydrocarbyl, substituted hydrocarbyl, heterohydrocarbyl or substituted heterohydrocarbyl; when any two or more of $R^1$ to $R^4$, $R^6$ and $R^{19}$ to $R^{28}$ are hydrocarbyl, substituted hydrocarbyl, heterohydrocarbyl or substituted heterohydrocarbyl, said two or more can be linked to form one or more cyclic substituents.

7. The composition according to claim 3 wherein the activator for the chain growth catalyst system is selected from organoaluminum compounds or hydrocarbylboron compounds.

* * * * *